US012357280B2

(12) United States Patent
Manning et al.

(10) Patent No.: US 12,357,280 B2
(45) Date of Patent: Jul. 15, 2025

(54) HEAT DISSIPATION IN ULTRASOUND PROBES

(71) Applicant: KONINKLIJKE PHILIPS N.V., Eindhoven (NL)

(72) Inventors: Ryan M Manning, Lewistown, PA (US); Dennis Dean Clark, Lewistown, PA (US); John William Myers, Lewistown, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2 days.

(21) Appl. No.: 18/284,127

(22) PCT Filed: Mar. 10, 2022

(86) PCT No.: PCT/EP2022/056179
§ 371 (c)(1),
(2) Date: Sep. 26, 2023

(87) PCT Pub. No.: WO2022/207268
PCT Pub. Date: Oct. 6, 2022

(65) Prior Publication Data
US 2024/0173017 A1    May 30, 2024

Related U.S. Application Data

(60) Provisional application No. 63/169,345, filed on Apr. 1, 2021.

(30) Foreign Application Priority Data

Jul. 23, 2021  (EP) ..................................... 21187391

(51) Int. Cl.
*A61B 8/00*    (2006.01)
*A61B 8/14*    (2006.01)

(52) U.S. Cl.
CPC ................ *A61B 8/546* (2013.01); *A61B 8/14* (2013.01)

(58) Field of Classification Search
CPC ........ A61B 8/4444; A61B 8/546; A61N 7/00; A61N 2007/0052
See application file for complete search history.

(56) References Cited

U.S. PATENT DOCUMENTS

| 5,213,103 A | 5/1993 | Martin et al. |
| 5,721,463 A | 2/1998 | Snyder et al. |

(Continued)

FOREIGN PATENT DOCUMENTS

| WO | 2012156886 A1 | 11/2012 | |
| WO | WO-2019185478 A1 * | 10/2019 | ........... A61B 8/4236 |

OTHER PUBLICATIONS

International Search Report and Written Opinion for PCT/EP2022/056179; Mailing date: Apr. 8, 2022, 10 pages.

*Primary Examiner* — Carolyn A Pehlke

(57) ABSTRACT

An ultrasound imaging device includes a housing with an outer surface and an inner surface. The outer surface is grasped by a user. The device includes an array of acoustic elements transmitting ultrasound energy and receiving ultrasound echoes. The array is at an end of the housing. The device includes a heat sink within the housing and receiving heat generated by the array. The device includes a heat pipe within the housing and transmitting the heat away from the end of the housing. The device includes a heat spreader material on the inner surface of the housing and dissipating the heat. The distal portion of the heat pipe is in thermal contact with the heat sink and the proximal portion of the heat pipe is in thermal contact with the heat spreader material. The proximal portion and the distal portion have a flattened profile.

13 Claims, 7 Drawing Sheets

(56) References Cited

U.S. PATENT DOCUMENTS

| | | | |
|---|---|---|---|
| 2006/0100513 A1* | 5/2006 | Hashimoto | G10K 11/004 600/437 |
| 2008/0146924 A1* | 6/2008 | Smith | G01S 7/52017 601/2 |
| 2012/0238880 A1 | 9/2012 | Davidsen et al. | |
| 2014/0364742 A1 | 12/2014 | Cho et al. | |
| 2015/0289852 A1 | 10/2015 | Cho et al. | |
| 2016/0174939 A1 | 6/2016 | Cho et al. | |
| 2017/0164926 A1 | 6/2017 | Spicci et al. | |
| 2019/0162832 A1* | 5/2019 | Otsuka | G01S 7/52079 |
| 2021/0059645 A1 | 3/2021 | Song et al. | |
| 2022/0000451 A1* | 1/2022 | Bryzek | B06B 1/0292 |

\* cited by examiner

HEAT DISSIPATION IN ULTRASOUND PROBES

CROSS-REFERENCE TO PRIOR APPLICATIONS

This application is the U.S. National Phase application under 35 U.S.C. § 371 of International Application No. PCT/EP2022/056179, filed on Mar. 10, 2022, which claims the benefit of U.S. Provisional Patent Application No. 63/169,345, filed Apr. 1, 2021, and European Patent Application No. 21187391.4, filed on Jul. 23, 2021. These applications are hereby incorporated by reference herein.)

TECHNICAL FIELD

The present disclosure relates generally to dissipating heat from an ultrasound probe. For example, a low resistance thermal path (e.g., within the housing of the ultrasound probe) connects the heat source with a large area heat spreader maximizing heat transfer away from the source.

BACKGROUND

Ultrasound imaging systems are widely used for medical imaging and measurement. For example, ultrasound imaging systems may be used to make measurements of organs, lesions, tumors, or other structures within a patient's anatomy. During ultrasound imaging procedures, a user of the ultrasound imaging system brings a probe into contact with the body of a patient. An array of elements within the probe emit acoustic energy into the patient and receive reflected waves used to construct an image of the patent anatomy. Many transducer arrays use piezo-electric materials to generate acoustic energy. While generating acoustic energy to transmit into the patent anatomy, these piezo-electric transducers and materials in the acoustic path also generate heat causing the temperature within the probe to rise. Increasing the amplitude of transmitted acoustic waves generally increases the quality of ultrasound images acquired by the ultrasound system, but increasing this amplitude also increases heat generated. If the temperature of the probe is not controlled, this heat may cause discomfort or physical harm to a patient.

Government regulations determine what amount of temperature rise within a medical ultrasound transducer is permissible. As a result, power transmitted to a medical ultrasound transducer is often limited by temperature rise. In addition, dissipating heat from an ultrasound probe has proven challenging because it is often generated within, and/or surrounded by, materials with low thermal conductivity.

US 2016/0174939 discloses an ultrasonic probe which has a heat absorbing backing layer, a heat spreader underneath the backing layer, and a heat pipe which extends between the heat spreader and a heat radiation plate to transfer heat to an exterior of the ultrasonic probe.

US 2021/059645 discloses an ultrasonic probe having a support structure using a thermally conductive material.

SUMMARY

The invention is defined by the claims.

Embodiments of the present disclosure are systems, devices, and methods for efficiently dissipating heat from an ultrasound transducer with a low resistance thermal path. As heat is generated by the transducer array, it may be absorbed and dissipated by a heatsink positioned behind the transducer array. The heatsink includes a set of fins extending from the heatsink towards the transducer array. These heatsink fins are embedded within an acoustic backing material with highly attenuative properties. One end of one or more heat pipes also contact the heatsink and extend along the length of the ultrasound probe. Heat may be transferred from the heatsink to these heat pipes via a thermal interface material. At the other end of the heat pipes, the pipes are brought into contact with a heat spreader material that is adhered to the inner surface of the ultrasound probe housing. Heat may pass from the heat pipes to the heat spreader material via additional thermal interface material, such as a gap filling paste. From the heat spreader material, heat may then be dissipated to the ultrasound probe housing and to the surrounding environment.

The low resistance thermal path described advantageously allows the transducer array of the ultrasound probe to emit higher power acoustic energy without exceeding regulatory limits on transducer face temperature. This results in a lower operating temperature and increased emitting power for the probe. The increased emitting power allows the ultrasound system to generate higher quality ultrasound data, which can improve how helpful the ultrasound data is for a physician making diagnostic and/or therapeutic decisions and therefore the patient's health.

In an exemplary aspect of the present disclosure, an ultrasound imaging device is provided. The device includes a housing comprising an outer surface and an inner surface, wherein the outer surface is configured to be grasped by a user: an array of acoustic elements configured to transmit ultrasound energy and receive ultrasound echoes associated with the ultrasound energy, wherein the array of acoustic elements is disposed at an end of the housing: a heat sink disposed within the housing and configured to receive heat generated by the array of acoustic elements: a heat pipe disposed within the housing and configured to transmit the heat away from the end of the housing, wherein the heat pipe comprises a proximal portion and a distal portion: and a heat spreader material disposed on the inner surface of the housing and configured to dissipate the heat, wherein the distal portion of the heat pipe is in thermal contact with the heat sink and the proximal portion of the heat pipe is in thermal contact with the heat spreader material, and wherein the proximal portion and the distal portion comprise a flattened profile.

In one aspect, the heat pipe comprises a bent shape. In one aspect, the heat spreader material comprises pyrolytic graphite. In one aspect, the device further includes an electrically conductive adhesive configured to adhere the heat spreader material to the inner surface of the housing. In one aspect, the device further includes electronics in communication with the array of acoustic elements and disposed within the housing, the inner surface of housing comprises a metallized portion forming a shield for the electronics against at least one of electromagnetic interference or radiofrequency interference, and the heat spreader material is in electrical communication with the metallized portion via the electrically conductive adhesive such that the heat spreader material comprises a portion of the shield. In one aspect, the heat sink comprises a body and a plurality of fins extending from the body, and the plurality of fins is disposed between the array of acoustic elements and the body. In one aspect, the device further includes an acoustic backing material disposed on a backside of the array of acoustic elements, and the plurality of fins are embedded within the acoustic backing material. In one aspect, the device further includes a thermal interface material, the distal portion of the heat pipe is in thermal contact with the body of the heat sink, and the thermal interface material is disposed between the distal portion of the heat pipe and the body of the heat sink. In one aspect, the device further includes a mounting bracket, the distal portion of the heat pipe is in thermal contact with the body of the heat sink, the distal portion of the heat pipe is coupled to the mounting bracket, and the mounting bracket is coupled to the body of the heat sink. In one aspect, the body of the heat sink comprises a curved portion, and the plurality of fins extend from the curved portion such that the plurality of fins comprise a curved profile. In one aspect, the heat pipe comprises a central portion between the proximal portion and the distal portion, the flattened profile of the proximal portion and the distal portion comprises a larger surface area for thermal contact, and the central portion comprises a non-flattened profile with a smaller surface area for thermal contact. In one aspect, the device further includes electronics in communication with the array of acoustic elements and disposed within the housing and a spacer disposed between the electronics and the heat pipe, and configured to urge the proximal portion of the heat pipe closer to the inner surface of the housing than the central portion of the heat pipe. In one aspect, the device further includes a thermal interface material disposed between the proximal portion of the heat pipe and the inner surface of the housing. In one aspect, the device further includes an additional heat pipe, the housing comprises a first portion coupled to a second portion, the proximal portion of the heat pipe is in thermal contact with the inner surface of the first portion of the housing, and a proximal portion of the additional heat pipe is in thermal contact with the inner surface of the second portion of the housing.

In an exemplary aspect of the present disclosure, an ultrasound imaging device is provided. The device includes a housing comprising an outer surface and an inner surface, wherein the outer surface is configured to be grasped by a user: an array of acoustic elements configured to transmit ultrasound energy and receive ultrasound echoes associated with the ultrasound energy, wherein the array of acoustic elements is disposed at an end of the housing: an acoustic backing material deposed on a backside of the array of acoustic elements; and a thermal path configured to drain heat generated by the array of acoustic elements away from the end of the housing and distribute the heat across at least one of the inner surface of the housing or the outer surface of the housing, wherein the thermal path comprises: a heat sink disposed within the housing, wherein the heat sink comprises a body and fins extending from the body toward the array of acoustic elements, wherein the fins are embedded in the acoustic backing material; a heat pipe comprising a bent shape to fit within the housing, wherein the heat pipe comprises a proximal portion and a distal portion; and a heat spreader material disposed on the inner surface of the housing, wherein the proximal portion of the heat pipe is in thermal contact with the body of the heat sink and the distal portion of the heat pipe is in thermal contact with the heat spreader material, and wherein the proximal portion and the distal portion comprise a flattened profile with a larger surface area for thermal contact.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
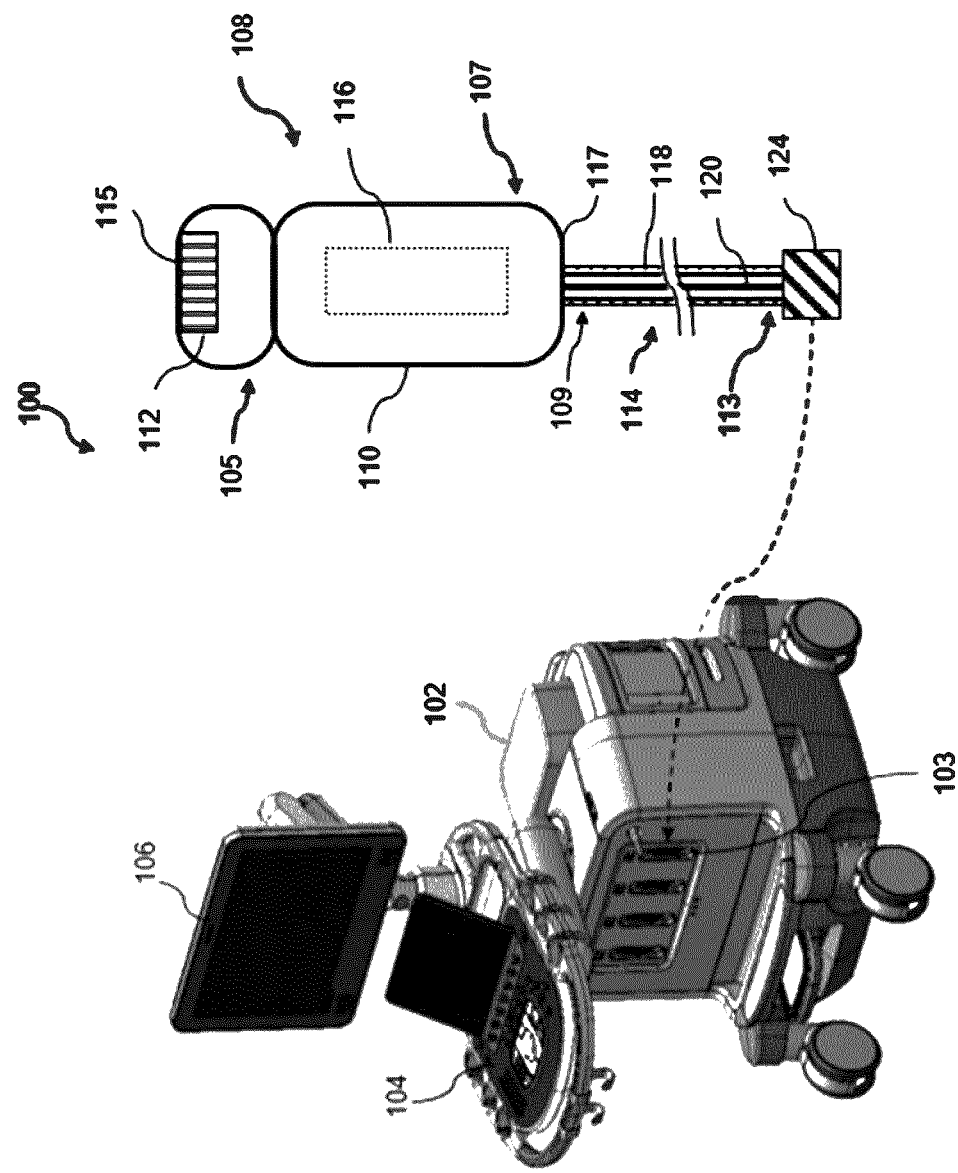
FIG. 1 is a diagrammatic perspective view of an ultrasound imaging system including a console and an ultrasound probe, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic perspective view of an ultrasound imaging system 100, according to aspects of the present disclosure. The ultrasound imaging system 100 includes a console 102 and an ultrasound probe 108. The ultrasound imaging system 100 may be used to obtain and display ultrasound images of anatomy. In some circumstances, the system 100 may include additional elements and/or may be implemented without one or more of the elements illustrated in FIG. 1.

The ultrasound probe 108 is sized and shaped, structurally arranged, and/or otherwise configured to be placed on or near the anatomy of a subject to visualize anatomy inside of the subject's body. The subject may be a human patient or animal. The ultrasound probe 108 may be positioned outside the body of the subject. In some embodiments, the ultrasound probe 108 is positioned proximate to and/or in contact with the body of the subject. For example, the ultrasound probe 108 may be placed directly on the body of the subject and/or adjacent to the body of the subject. The view of the anatomy shown in the ultrasound image depends on the position and orientation of the ultrasound probe 108. To obtain ultrasound data of the anatomy, the ultrasound probe 108 can be suitably positioned and oriented by a user, such as a physician, sonographer, and/or other medical personnel, so that a transducer array 112 emits ultrasound waves and receives ultrasound echoes from the desired portion of the anatomy. The ultrasound probe 108 may be portable and suitable for use in a medical setting. In some instances, the ultrasound probe 108 can be referenced as an ultrasound imaging device, a diagnostic imaging device, external imaging device, transthoracic echocardiography (TTE) probe, and/or combinations thereof.

The ultrasound probe 108 includes a housing 110 structurally arranged, sized and shaped, and/or otherwise configured for handheld grasping by a user. The housing 110 can be referenced as a handle in some instances. A proximal portion 107 of the housing 110 can be referenced as a handle in some instances. The housing 110 surrounds and protects the various components of the imaging device 108, such as electronic circuitry 116 and the transducer array 112. Internal structures, such as a space frame for securing the various components, may be positioned within the housing 110. In some embodiments, the housing 110 includes two or more portions which are joined together during manufacturing. The housing 110 can be formed from any suitable material, including a plastic, a polymer, a composite or combinations thereof.

The housing 110 and/or the ultrasound probe 108 includes the proximal portion 107 terminating at a proximal end 117 and a distal portion 105 terminating at a distal end 115. In some instances, the ultrasound probe 108 can be described as having the proximal portion 107 and the distal portion 105. An imaging assembly of the ultrasound probe 108, including the transducer array 112, is disposed at the distal portion 105. All or a portion of the imaging assembly of the ultrasound probe 108 can define the distal end 115. The transducer array 112 can be directly or indirectly coupled to the 35 housing 110. The operator of the ultrasound probe 108 may contact the distal end 115 of the ultrasound probe 108 to the body of the patient such that the anatomy is compressed in a resilient manner. For example, the imaging assembly, including the transducer array 112, may be placed directly on or adjacent to the body of the subject. In some instances, the distal portion 105 is placed directly in contact with the body of the subject such that the transducer array 112 is adjacent to the body of the subject.

The ultrasound probe 108 is configured to obtain ultrasound imaging data associated with any suitable anatomy of the patient. For example, the ultrasound probe 108 may be used to examine any number of anatomical locations and tissue types, including without limitation, organs including the liver, heart, kidneys, gall bladder, pancreas, lungs: ducts: intestines: nervous system structures including the brain, dural sac, spinal cord and peripheral nerves: the urinary tract: as well as valves within the blood vessels, blood, chambers or other parts of the heart, and/or other systems of the body. The anatomy may be a blood vessel, such as an artery or a vein of a patient's vascular system, including cardiac vasculature, peripheral vasculature, neural vasculature, renal vasculature, and/or any other suitable lumen inside the body. In addition to natural structures, the ultrasound probe 108 may be used to examine man-made structures such as, but without limitation, heart valves, stents, shunts, filters and other devices.

The transducer array 112 is configured to emit ultrasound signals, and receive ultrasound echo signals corresponding to the emitted ultrasound signals. The echo signals are reflections of the ultrasound signals from anatomy with the subject's body. The ultrasound echo signals may be processed by the electronic circuitry 116 in the ultrasound probe 108 and/or in the console 102 to generate ultrasound images. The transducer array 112 is part of the imaging assembly of the ultrasound probe 108, including an acoustic window/lens and a matching material on a transmitting side of the transducer array 112, and an acoustic backing material on a backside of the transducer array 112. The acoustic window and the matching material have acoustic properties that facilitate propagation of ultrasound energy in desired directions (e.g., outwards, into the body of the patient) from the transmitting side of the transducer array 112. The backing material has acoustic properties that impede or limit propagation of ultrasound energy in undesired directions (e.g., inwards, away from the body of the patient) from the backside of the transducer array 112.

The transducer array 112 may include any number of transducer elements. For example, the array can include between 1 acoustic element and 10000 acoustic elements, including values such as 2 acoustic elements, 4 acoustic elements, 15 acoustic elements, 64 acoustic elements, 128 acoustic elements, 500 acoustic elements, 812 acoustic elements, 3000 acoustic elements, 9000 acoustic elements, and/or other values both larger and smaller. The transducer elements of the transducer array 112 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., arranged in one or more rows, one or more columns, and/or one or more orientations) can be uniformly or independently controlled and activated. The transducer array 112 can be configured to obtain one-dimensional, two-dimensional, and/or three-dimensional images of patient anatomy. The ultrasound transducer elements may be piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The transducer array 112 is in communication with (e.g., electrically coupled to) the electronic circuitry 116. The electronic circuitry 116 can be any suitable passive or active electronic components, including integrated circuits (ICs), for controlling the transducer array 112 to obtain ultrasound imaging data and/or processing the obtained ultrasound imaging data or one or more printed control boards (PCBs). For example, the electronic circuitry 116 can include one or more transducer control logic dies. The electronic circuitry 116 can include one or more application specific integrated circuits (ASICs). In some embodiments, one or more of the ICs can comprise a microbeamformer (μBF), an acquisition controller, a transceiver, a power circuit, a multiplexer circuit (MUX), etc. In some embodiments, the electronic circuitry 116 can include a processor, a memory, a gyroscope, and/or an accelerometer. The electronic circuitry 116 may include a PCB 270 as shown. Various electrical components 272, including but not limited to resistors, capacitors, transistors, any of the components previously mentioned, or any other electrical components may be mounted to the PCB. The electronic circuitry 116 including the PCB 270 and electrical components 272 are disposed within the ultrasound probe 108 and surrounded by the housing 110.

The ultrasound probe 108 includes a cable 114 to provide signal communication between the console 102 and one or more components of the ultrasound probe 108 (e.g., the transducer array 112 and/or the electronic circuitry 116). The cable 114 includes multiple electrical conductors 120 configured to carry electrical signals between the console 102 and the ultrasound probe 108. The electrical conductors 120 can be bare wires surrounded by one or more layers of insulating materials. The insulating materials are typically polymer-based composites, nylon, and/or polyvinyl chloride (PVC) synthetic plastic polymer. In some embodiments, the conductors may be coaxial. The coaxial structures may use PTFE or expanded PTFE inner dielectrics and outer dielectrics of PET or PTFE. For example, electrical signals representative of the imaging data obtained by the transducer array 112 can be transmitted from the ultrasound probe 108 to the console 102 via the electrical conductors 120. Control signals and/or power can be transmitted from the console 102 to the ultrasound probe 108 via the electrical conductors 120. The cable 114 and/or electrical conductors 120 may provide any type of wired connection, such as a proprietary connection, an Ethernet connection, a Universal Serial Bus (USB) connection of any version or a mini USB of any version.

The cable 114 can also include a conduit 118 surrounding the electrical conductors 120. The conduit 118 is shaped as a tube and used to protect and route the electrical conductors 120 in the cable 114 of the ultrasound imaging device 108. The conduit 118 can be flexible and made of polymer, plastic, metal, fiber, other suitable materials, and/or combinations thereof. The conduit 118 protects the electrical conductors 120 by preventing their direct exposure to outside elements. A distal portion 109 of the cable 114 is coupled to the proximal portion 107 of the housing 110 of the ultrasound probe 108.

A connector 124 is located at a proximal portion 113 of the cable 114. The connector 124 is configured for removably coupling with the console 102. Signal communication between the ultrasound probe 108 and the console 102 is established when the connector 124 is received within a receptacle 103 of the console 102. In that regard, the ultrasound probe 108 can be electrically and/or mechanically coupled to the console 102. The console 102 can be referenced as a computer or a computing device in some instances. The console 102 includes a user interface 104 and a display 106. The console 102 is configured to process the ultrasound imaging data obtained by the ultrasound probe 108 to generate an ultrasound image and output the ultrasound image on the display 106. A user can control various aspects of acquiring ultrasound imaging data by the ultrasound probe 108 and/or display of ultrasound images by providing inputs at the user interface 104. The imaging device 108 and the display 106 may be communicatively coupled directly or indirectly to the console 102.

One or more image processing steps can be completed by the console 102 and/or the ultrasound probe 108. The console 102 and/or the ultrasound probe 108 can include one or more processors in communication with memory. The processor may be an application-specific integrated circuit (ASIC), a field-programmable gate array (FPGA), a central processing unit (CPU), a digital signal processor (DSP), another hardware device, a firmware device, or any combination thereof configured to perform the operations described herein. In some embodiments, the memory is a random access memory (RAM). In other embodiments, the memory is a cache memory (e.g., a cache memory of the processor), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory may include a non-transitory computer-readable medium. The memory may store instructions. The instructions may include instructions that, when executed by a processor, cause the processor to perform operations described herein.

While the console 102 is a movable cart in the illustrated embodiment of FIG. 1, it is understood that the console 102 can be a mobile device (e.g., a smart phone, a tablet, a laptop, or a personal digital assistant (PDA)) with integrated processor(s), memory and display. For example, a touchscreen of the mobile device can be the user interface 104 and the display 106.

Figure 2:
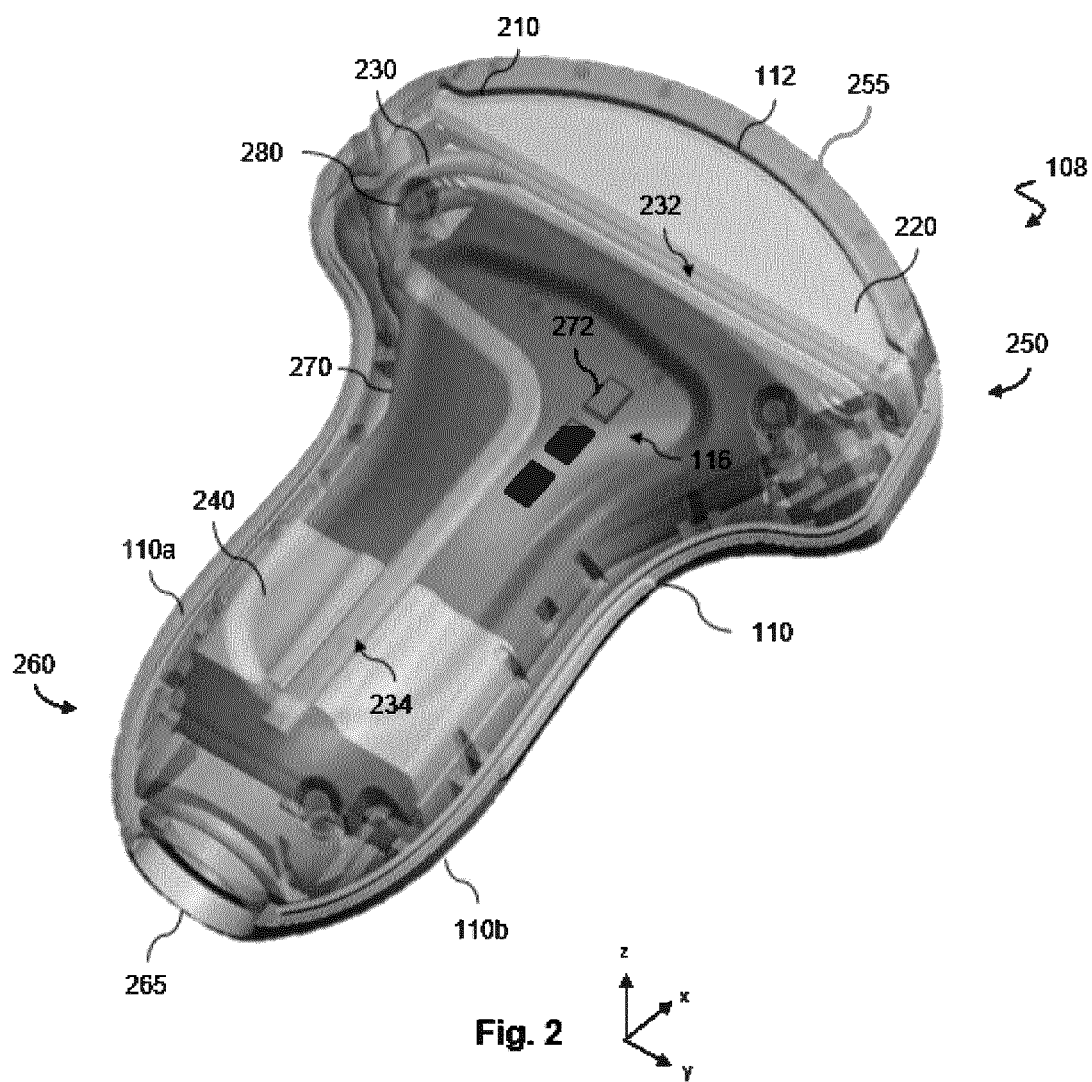
FIG. 2 is a partially transparent perspective view of an ultrasound probe, according to aspects to aspects of the present disclosure.

FIG. 2 is a partially transparent perspective view of an ultrasound probe 108, according to aspects to aspects of the present disclosure. FIG. 2 depicts exemplary embodiments of the transducer array 112, the probe housing 110, and the electronic circuitry 116 previously described with reference to FIG. 1. In addition. FIG. 2 depicts an acoustic backing material 210, a heatsink 220, a heat pipe 230, and a spacer 240.

As shown in FIG. 2, the transducer array 112 may be disposed at the distal portion 250 of the probe housing 110 near the distal end 255 and may be of any suitable type as described with reference to FIG. 1. The housing 110 also includes a proximal region 260 and proximal end 265 as shown. The acoustic backing material 210 may be disposed proximal to the transducer array 112 and distal to the heatsink 220. One purpose of the acoustic backing material is to absorb acoustic energy generated by the transducer array 112, which may propagate in a proximal direction from the transducer array 112. Additional features of the acoustic backing material 210 will be described with more detail with reference to FIG. 3 hereafter.

The probe housing 110 may include multiple portions. For example, as shown in FIG. 2, the housing 110 may include two portions, a housing portion 110a, shown as a partially transparent component in FIG. 2, and a housing portion 110b, shown as a solid component in FIG. 2 and positioned opposite the portion 110a.

The heatsink 220 may be positioned proximal to the acoustic backing material 210. The heatsink 220 may be disposed in the housing 110 such that it is positioned near the transducer array 112. A purpose of the heatsink 220 is to absorb heat generated by the transducer array 112 and/or the backing material 210, and dissipate that heat to other portions of the probe 108 as will be discussed with more detail hereafter. In some embodiments, the transducer array 112 may be constructed of piezo-electric crystals to produce acoustic energy. These piezo-electric crystals may also generate heat which may be transmitted to a patient's body in excess of regulatory limits on the permissible temperatures of ultrasound probes. The transducer array 112 can be a source of heat within the probe 108. In many applications, the transducer array 112 itself may not be constructed of thermally conductive materials. In addition, other components within the probe, such as an acoustic lens or other materials relating to the transducer array 112, may be constructed of materials that are not thermally conductive (e.g. polymers or ceramics). The heatsink 220 may, therefore, be constructed of a thermally conductive material and may more efficiently dissipate heat away from the transducer array 112 before the probe temperature reaches disallowed levels.

In general, the heat pipe 230 transmits heat away from the heat source(s), such as the transducer array 112 and/or the acoustic backing material 210, at the distal portion 250 and/or the distal end 255 of the probe housing 110. The heat pipe 230 shown in FIG. 2 may include a distal portion 232 and a proximal portion 234. The heat pipe 230 may also be referred to as a thermal pipe. The distal portion 232 of the heat pipe 230 is mechanically and thermally coupled to the heatsink 220. The proximal portion 234 of the heat pipe 230 is mechanically and thermally coupled to a heat spreader material within the housing 110 as will be described with more detail hereafter. A purpose of the heat pipe 230 is to efficiently transfer heat from the heatsink 220 to the heat spreader material. As shown, the heat pipe 230 may be formed in a bent shape to make space for or avoid other components within the housing 110 such as the circuitry 116, the PCB 270 or electrical components 272. In some embodiments, the heat pipe 230 may be shaped in such a way to bend around one or more fastener structures such as screw receivers 280 or other structures, parts, or components within the housing 110.

The spacer 240 may be disposed within the housing 110 near the proximal portion 234 of the heat pipe 230 and may urge the proximal portion 234 of the heat pipe 230 into contact with the heat spreader material which may be positioned on the inner surface of the housing 110. Additional aspects of the spacer 240, as well as the heat spreader material, will be described in more detail hereafter.

It is noted that the probe 108 may include any suitable number of heat pipes 230 in addition to the heat pipe 230 shown in FIG. 2. For example, one additional heat pipe 230 may be positioned within the probe 108 of a similar shape as the heat pipe 230 shown. This additional heat pipe 230 may be positioned on the opposite side of the electronic circuitry 116 shown and will be discussed with more detail with reference to FIG. 3. It will be apparent that, in additional embodiments, additional heat pipes 230 may be positioned in contact with both the heatsink 220 and the heat spreader material by altering various geometries, placements, and/or configurations of various components within the housing 108. Any heat pipe 230 shown or described may also be of any suitable shape.

Figure 3:
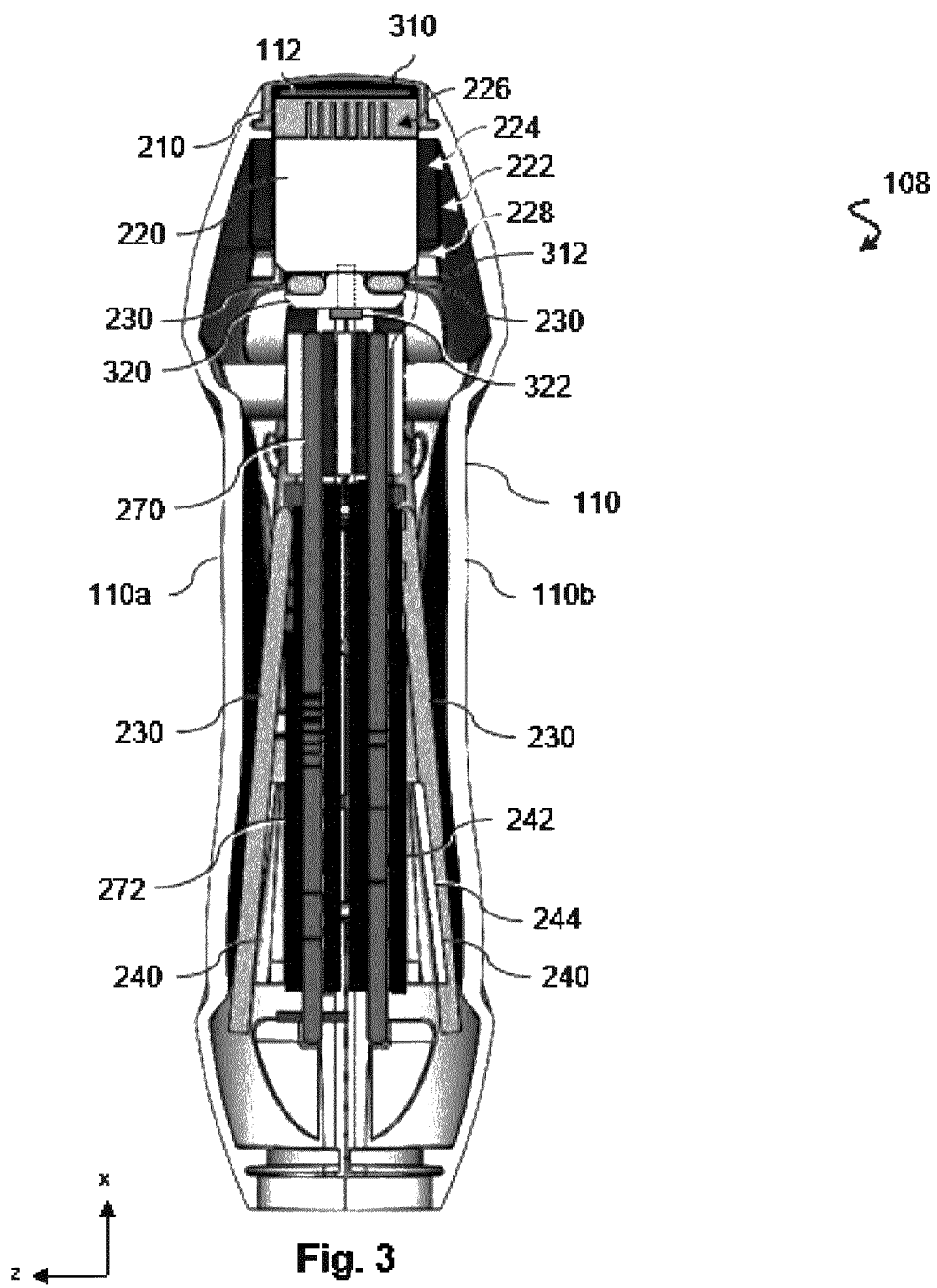
FIG. 3 is a diagrammatic cross-sectional side view of the ultrasound probe, according to aspects of the present disclosure.

FIG. 3 is a diagrammatic cross-sectional side view of the ultrasound probe 108, according to aspects of the present disclosure. The view of the ultrasound probe 108 in FIG. 3 is along a plane defined by the x-axis and the z-axis. FIG. 3 depicts the acoustic backing material 210 and the heatsink 220 including a heatsink body 222 and heatsink fins 226. FIG. 3 additionally depicts the transducer array 112, an acoustic lens 310, the heat pipes 230 extending within the interior of the probe housing 110, the spacer 240, a mounting bracket 320, and a machine screw 322. A coordinate system indicator 390 is also shown. The indicator 390 indicates the x-axis and the z-axis.

The acoustic backing material 210 may be disposed on the backside of the transducer array 112 of acoustic elements. The acoustic backing material 210 may additionally be referred to as absorptive material, acoustic insulating material, or any other suitable term. The backing material 210 may be selected to absorb acoustic energy generated by the transducer array 112. In this way, the backing material 210 may prevent acoustic energy from propagating in a direction proximal to the transducer array 112 and/or prevent acoustic energy that may be received by the transducer array 112 from a proximal direction, resulting in more accurate ultrasound data. The acoustic backing material may be constructed of any suitable material including but not limited to epoxy or thermoplastic resins with or without fillers to enhance dissipation of ultrasonic energy. In some embodiments, because the acoustic backing material 210 is positioned directly adjacent to the transducer array 112, the material 210 may conform to a similar shape as the transducer array 112 but may also be of any suitable shape or size.

In some embodiments, heat may also be generated by interaction between sound waves and the acoustic backing material 210, such that the acoustic backing material 210 can be a source of heat within the probe 108.

The backing material 210 is positioned distal to the heatsink 220, as shown. The heatsink 220 may additionally be referred to as a dissipater. The heatsink 220 may also be of any suitable shape or size. The heatsink 220 may be constructed of a thermally conductive material and can be a non-metal, metal, or metal alloy, such as silver, copper, gold, aluminum nitride, silicon carbide, aluminum, tungsten, graphite, zinc, other suitable materials, and/or combinations thereof. Given the high thermal conductivity of the heatsink 220, the heatsink may efficiently transfer heat from the transducer array 112 to the heat pipes 230.

In some embodiments, the heatsink 220 may include a body 222 and a number of fins 226. The heatsink body 222 has a proximal region 228 and a distal region 224. The fins 226 may extend from the distal region 224 of the body 222. The heatsink 220 may include any suitable number of fins 226. The fins 226 may also be of any suitable shape, pattern, length, or may extend from the body 222 according to any suitable path. In some embodiments, the fins 226 may extend distally from the heatsink body 222 towards the transducer array 112. For example, the fins 226 may be placed between the transducer array 112 and the heatsink body 222. The set of fins 226 of the heatsink 220 may be embedded within the acoustic backing material 210 as shown in FIG. 2. The acoustic backing material 210 may surround each of the fins 226 such that every exterior point of the fins 226 are in contact with the acoustic backing material. In some embodiments, the acoustic backing material 210 may be a resin that is cast on the fins 226.

Because the effectiveness of the heatsink 220 depends on both the distance between the heatsink fins 226 and the transducer array and the length of the heatsink fins 226 themselves, the acoustic backing material 210 may be selected to be of a highly attenuative material. For example, the attenuation of the acoustic backing material 210 may be at least 15 dB/mm or greater than 15 dB/mm. By using a highly attenuative material for the acoustic backing material 210, less material 210 is needed to sufficiently attenuate unwanted acoustic energy and the layer of material 210 between the transducer array 112 and the heatsink body may be thinner. A thinner layer of backing material 210 allows for shorter, and therefore more effective, heatsink fins 226. These shorter fins 226 reduce thermal resistance between the heat source (e.g. the transducer array 112) and the body 222 of the heatsink 220. The fins 226 of the heatsink 220 may be spaced from the transducer array 112 by some distance. The fins 226 may be positioned very close to the transducer array 112 to optimize heat dissipation from the transducer array 112. For example, the distal ends of the fins 226 may be positioned within 1 mm or less of the transducer array 112.

Figure 4:
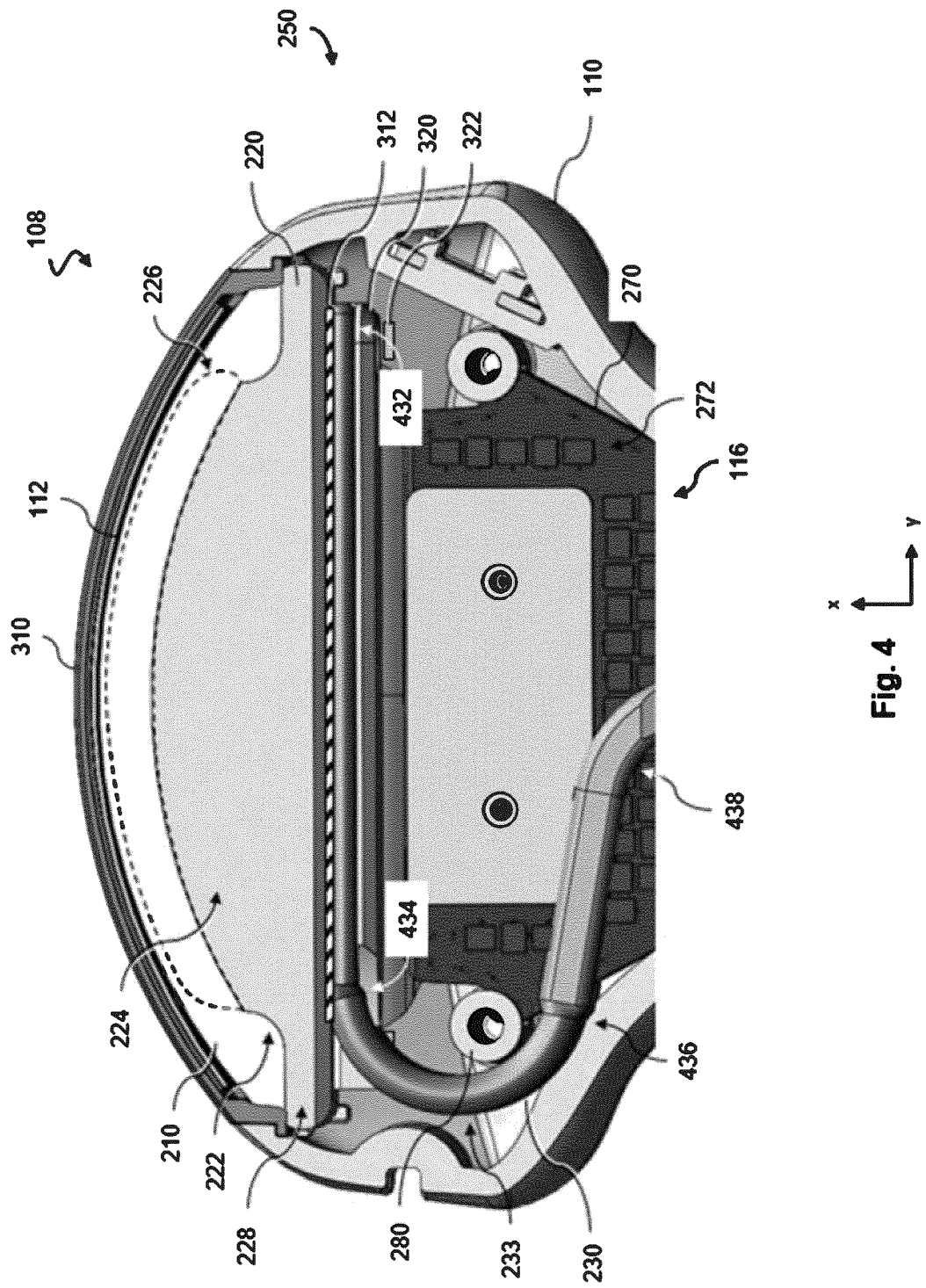
FIG. 4 is a diagrammatic cross-sectional front or back view of a distal portion of an ultrasound probe, according to aspects of the present disclosure.

As shown in FIG. 4, the body 222 of the heat sink 220 may include a curved upper portion 224. The distal edge of this curved upper portion 224 may be of substantially the same curvature as the transducer array 112 and acoustic lens 310 of the probe 108. FIG. 4 additionally depicts fins 226 extending distally from the curved upper portion 224 within the backing material 210.

FIG. 3 additionally depicts the heat pipes 230. The heat pipes 230 may be configured to drain heat from the device 108. A cross section of the distal portion 232 of each heat pipe 230 is shown adjacent to the proximal region 228 of the heatsink body 222 and may be in physical and/or thermal contact with the heatsink 220. A thermal interface material 312 may be disposed between the distal portion 232 of the heat pipes 230 and the proximal region 228 of the heat sink 220. Like the heatsink 220, the heat pipes 230 may also be constructed of a thermally conductive material. For example, the heat pipes 230 may be constructed of aluminum or copper with water or ammonia as the working fluid. Additionally, the heat pipes 230 may include various components and/or structures. For example, in some embodiments, the heat pipes 230 may each include an envelope forming the exterior of the heat pipe 230 and constructed of a highly thermally conductive material. The envelope may enclose a wick structure and a working fluid. The wick structure may be affixed to the inner walls of the envelope and may absorb and distribute the working fluid along the heat pipe. The wick may be constructed of any suitable material and may be porous metal structure including, but not limited to copper, aluminum, or other materials. The working fluid in the heat pipes 230 may be distilled water. In other embodiments, the working fluid may alternatively be ammonia, nitrogen, acetone, methanol, methylamine, pentane, propylene, or any other suitable working fluids.

The heat pipes 230 may be shaped in such a way so that the distal region 232 of the heat pipes 230 are physically and/or thermally coupled to the proximal portion 228 of the heatsink 220, as shown in FIG. 3. Additional features and aspects of the shape and positioning of the heat pipes 230 will be described in more detail with reference to FIG. 4 and FIG. 5. However, as shown in FIG. 3, the distal portion 232 of the heat pipes 230 may be brought into physical contact with the proximal portion 228 of the heatsink 220 by a mounting bracket 320. The mounting bracket 320 may be shaped so as to allow a space through which the heat pipes 230 may extend proximate to the heat sink body 222. The heat pipes 230 may therefore be brought into contact with the heatsink 220 and then the mounting bracket 320 may be placed over the heat pipes and secured to the heatsink 220 via one or more machine screws 322. The heatsink 220 may include one or more threaded holes into which the one or more machine screws 322 may be received and tightened bringing the mounting bracket 320 into firm contact with the heat pipes 230 and/or the heatsink 220 and securing or coupling the heat pipes 230 to the heatsink 220. The mounting bracket 320 may be constructed of the same material as the heatsink 220 and/or the heat pipes 230 or may be constructed of a different material.

In some embodiments, the heat pipes 230 may be additionally or alternatively coupled to the heatsink 220 via soldering or a thermally conductive epoxy. In some embodiments, the bracket 320 may be omitted. The heat pipes 230 may be both mechanically and thermally coupled to the heatsink 220 and/or the bracket 320. In such an embodiment, the solder or thermally conductive epoxy may completely surround the outer surface of the distal portion 232 of the heat pipes 230 or may be in contact with only a portion of the heat pipes 230. In some embodiments, a thermal interface material may also be positioned between the heat pipes 230 and the heatsink 220 as will be described in more detail with reference to FIG. 4.

At their proximal portion 234, the heat pipes 230 may be pushed outward, or away from the centerline or central longitudinal axis of the probe 108 by the spacers 240 shown in FIG. 3. For example, in some embodiments, the proximal region 234 of the heat pipes 230 may gradually slope outward towards the housing 110 as the heat pipes 230 extend away from the heatsink 220. The spacers 240 may bring the proximal portion 234 of the heat pipes 230 into physical and/or thermal contact with the inner surface of the housing 110 and/or a heat spreader material on the inner surface of the housing 110. The spacers 240 may include an inner surface 242 positioned facing the centerline of the probe 108 and an outer surface 244 facing the exterior of the probe 108. The spacers 240 may be positioned in such a way that the heat pipes 230 are positioned at a distance from the PCB 270 and electronic components 272 as shown. In this way, the inner surface 242 of the spacer 240 may be in physical contact with the PCB 270 and electronic components 272 mounted to the PCB 270. The outer surface 244 of the spacers 240 may be in physical contact with the heat pipes 230. In this way, the spacers 240 separate the heat pipes 230 from the PCB 270 and electronic components 272.

Figure 5:
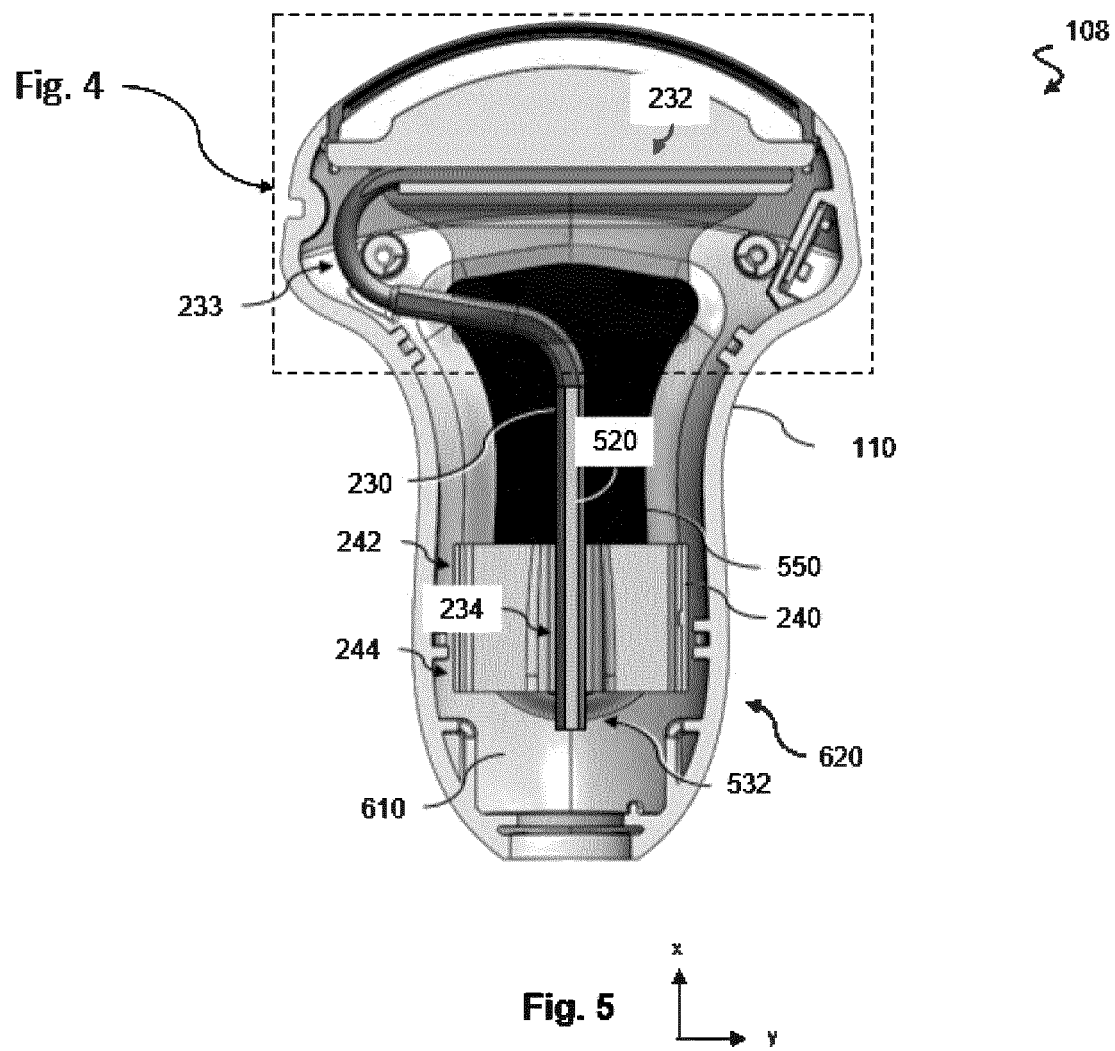
FIG. 5 is a diagrammatic cross-sectional front or back view of an ultrasound probe, according to aspects of the present disclosure.

FIG. 4 is a diagrammatic cross-sectional front or back view the ultrasound probe 108, according to aspects of the present disclosure. FIG. 4 will be described in connection with FIG. 5 which is a diagrammatic cross-sectional front or back view of the ultrasound probe 108, according to aspects of the present disclosure. The view of the ultrasound probe 108 in FIGS. 4 and 5 are along a plane defined by the x-axis and the y-axis. FIG. 4 depicts a distal region 250 of the probe 108 and shows, among other components, the acoustic lens 310, the transducer array 112, acoustic backing material 210, the heatsink 220, thermal interface material 312, a heat pipe 230 with several different regions, the screw receiver 280, the mounting bracket 320, machine screws 322, circuitry 116 including the PCB 270 and electronic components 272, and the housing 110.

As shown in FIG. 4, the body 222 of the heatsink 220 has a proximal region 228 and a distal or curved region 224. The fins 226 may extend from the distal region 224 of the curved region 224 into the acoustic backing material 210 and may form a curved profile as shown by the curved dotted lines in FIG. 4. In other embodiments, the transducer array 112 may not form a curved profile. For example, as mentioned with reference to FIG. 1, the transducer array 112 may be linear or planar. In such embodiments, the heatsink 220 and heatsink fins 226 may not be curved but may be positioned close to the transducer array 112 and may be of a linear or planar profile.

A thermal interface material 312 may be positioned between the proximal portion 228 of the heatsink 220 and the distal outer surface of the heat pipe 230, as shown. This thermal interface material 312 may also be referred to as a film. The material 312 may be a silicon-based material or any other suitable material. In some embodiments, the thermal interface material may include commercially available materials such as 3M Tape 8810, Berquist HF300P-0.004-00-10.5/250, or other materials. In some embodiments, the material 312 may be a cure-in-place material. The material 312 may be a die cut graphite sheet. The material 312 may be pliable and may ensure that the heatsink 220 and heat pipe 230 are brought into good thermal contact. The material 312 may also minimize air gaps between the surface of the heatsink 220 and the heat pipe 230. With relation to the heatsink 220, the thermal interface material 312 may be positioned on the opposite side of the heatsink 220 as the fins 226 of the heatsink 220.

As shown in FIG. 4, the heat pipe 230 may include a region 432, a region 434, a region 436, and a region 438. The distal portion 232 of the heat pipe 230 between region 432 and region 434 may extend along a surface of the heatsink 220. Along this distal portion 232, the heat pipe 230 may be of a flattened profile to maximize the surface area of the heat pipe 230 in contact with the heatsink 220 and/or the thermal interface material 312 to optimize heat transfer at this transition point. As shown in FIG. 3, the cross-sectional shape of the heat pipe 230 along this portion between region 432 and region 434 may be an oval shape with flat top and bottom surfaces. In other embodiments, the cross-sectional shape may differ.

At the region 434, the heat pipe 230 may curve away from the heatsink 220. The heat pipe 230 may then curve around other components such as circuitry 116 or other structures or components within the probe 108. Along this curved or central portion 233 between region 434 and region 436, the heat pipe 230 may not be flattened. The cross-sectional shape of the heat pipe 230 may be substantially circular from the region 434 to the region 436. The cross-sectional shape may also differ. Because the cross-sectional shape of the heat pipe 230 is circular at the central region 233, the surface area of the central portion 233 is less than the surface area of the heat pipes 230 at either the distal region 232 or the proximal region 234.

From the region 436 to the region 438 and extending along the proximal portion 234 of the heat pipe to the region 532 shown in FIG. 5, the heat pipe 230 may be of a flattened profile similar to the distal region 232 extending from region 432 to region 434. For example, the cross-sectional shape of the heat pipe 230 from region 436 to region 532 (FIG. 5) may be a similar shape as the cross-sectional shape from the region 432 to region 434, such as an oval with flat top and bottom surfaces, or any other suitable shape. This flattening from region 436 to region 532 (FIG. 5) may maximize the surface area of the heat pipe 230 brought into contact with the heat spreader material and/or the inner wall of the housing 110 to optimize heat transfer at this junction.

Figure 6:
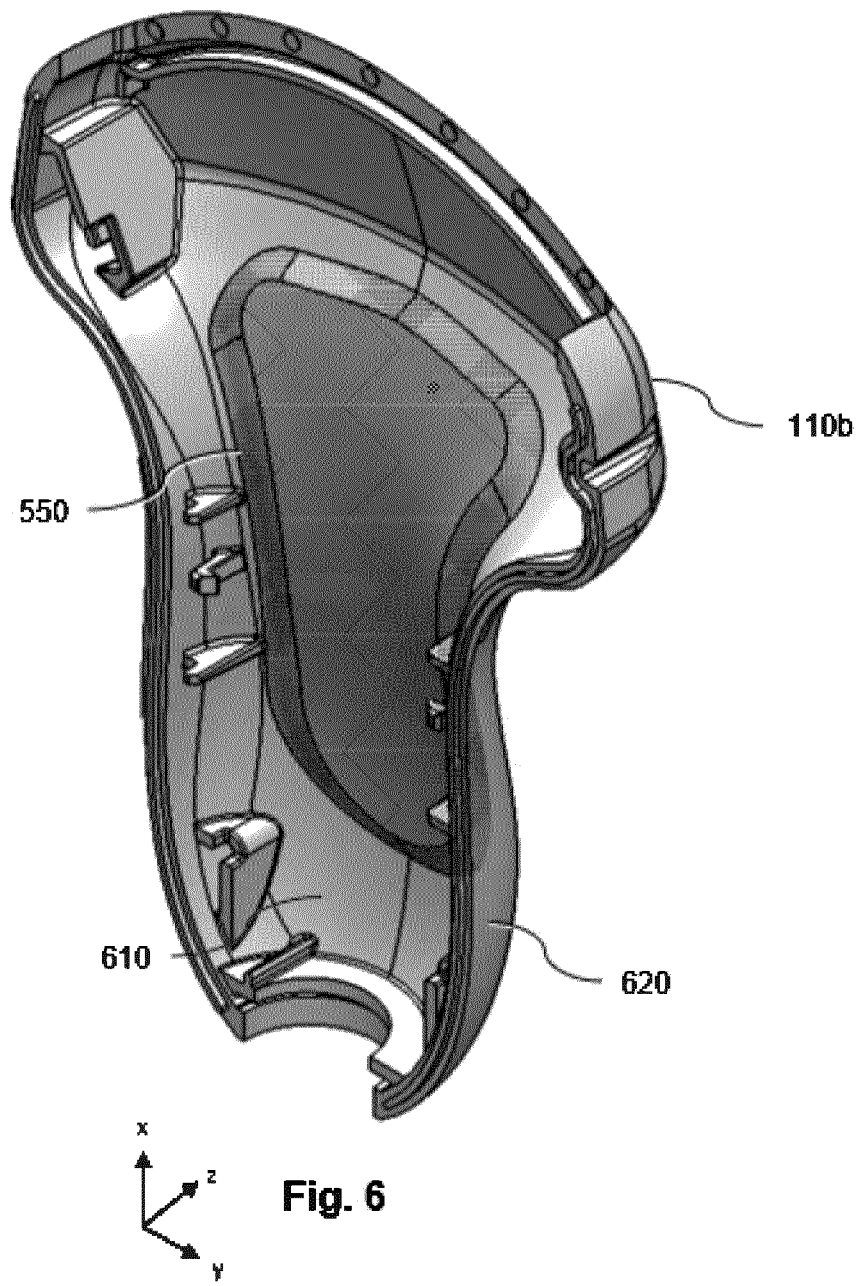
FIG. 6 is a diagrammatic perspective view of a portion of an ultrasound probe housing, according to aspects of the present disclosure.

The probe housing 110 may include an inner surface 610 and an outer surface 620 as shown in FIG. 5 and FIG. 6. The heat spreader material 550 shown in FIG. 5 may be adhered to the inner surface 610 of the housing 110. FIG. 5 also includes the coordinate system indicator 490 again indicating the x-axis and the y-axis. In some embodiments, the housing 110 may include two structures (e.g., two halves), portion 110a and portion 110b as described with reference to FIG. 2, similar to the housing portion 110b shown in FIG. 6, that are bonded together. The housing 110 may fully or partially enclose one or more of the components discussed herein. A heat spreader material 550 can be coupled to the inner surface of each housing portion that together forms the housing 110. In this way, one of the heat pipes 230 shown in FIG. 3 may be in physical and/or thermal contact with one heat spreader material 550 of one housing structure and the other heat pipe 230 of FIG. 3 may be in physical and/or thermal contact with the other heat spreader material 550 of the other housing structure.

The heat spreader material 550 may be configured to efficiently dissipate heat. The element 550 may be constructed of a thermally conductive material such as a pyrolytic graphite sheet. The element 550 may also be constructed of any other suitable material such as copper, aluminum including for example aluminum 1100, or other materials which have high thermal conductivity, other suitable planar thermally conductive materials, and/or combinations thereof. The heat spreader material 550 may also be referred to as a heat spreader, a heat dissipater, a heat spreader material, or any other suitable term. The heat spreader material 550 may be laminated to the inner surface of the housing 110. For example, an adhesive may be positioned on one side of the heat spreader material 550 that is placed in contact with the inner surface 610 of the housing portion 110a and/or 110b. The element 550 may be of any suitable size or shape. The element 550 may follow the inner contours of the housing 110. The element 550 may be configured to be as large as possible, or to be in contact with the most surface area of the housing 110 inner surface as possible to optimize heat transfer from the element 550 to the housing 110 and subsequently to the outside environment.

A thermal interface material 520 may be placed between the proximal region 234 of the heat pipe 230 and the heat spreader material 550 with which the pipe 230 is brought into physical and/or thermal contact. In some embodiments, this thermal interface material 520 is a thermally conductive and facilitates heat transfer between the heat pipe 230 and the heat spreader material 500 similar to how the thermal interface material 312 described with reference to FIG. 4 facilitates heat transfer between the distal portion 232 of the heat pipe 230 and the proximal portion 228 of the heatsink 220. In some embodiments, the thermal interface material 520 may be substantially similar to the thermal interface material 312. In other embodiments, the thermal interface material 520 may differ from the thermal interface material 312. The thermal interface material 520 and/or 312 may also be referred to as gap filling paste, thermal interface paste, gap filling material, filler material, interface material, or any other suitable term.

In some embodiments, the thermal interface material 520 can be a gap filling paste applied between the proximal portion 234 of the heat pipe 230 (e.g. from the region 438 of the pipe 230 to the region 532) and the heat spreader material 550. The thermal interface material 520 may be thermally conductive. In some embodiments, the material 520 may have adhesive properties to secure the proximal portion 234 of the heat pipe 230 to the heat spreader material 550. In some embodiments, after the spacers 240 are positioned adjacent to the heat pipes 230 during assembly and before the housing structures 110a and 110b are seated together to enclose the inner components, the spacers 240 may force the proximal region 234 of the heat pipes 230 outward such that they protrude outward along the z-axis farther than the housing 110 would permit. As a result, the act of seating the two structures 110a and 110b of the housing 110 on the assembly pushes the proximal region 234 of the heat pipes inward along the z-axis and compresses the spacers 240, thus applying pressure to the heat pipes 230 and forming secure contact with the heat spreaders 550. As the spacers 240 force the proximal region 234 of the heat pipes 230 into tighter contact with the heat spreader material 550, the thermal interface paste 520 flows and displaces resulting in a large area over which the proximal region 234 of the heat pipes 230 may contact with the pyrolytic heat spreaders 550. One purpose of the thermal interface material 520 may be to fill any air gaps between the heat pipes 230 and the spreaders 550 to maximize thermal transfer. Any suitable amount of thermal interface material 520 may be positioned between the pipes 230 and spreaders 550. In some embodiments, approximately 3-4 mm of thermal interface material is positioned between the proximal portion 234 of the pipes 230 and the heat spreaders 550.

FIG. 5 additionally depicts the spacer 240 mentioned previously. As shown in FIG. 3, one spacer 240 may be placed on the inner side of the proximal portion 234 of each of the heat pipes 230. In this way, a single heat pipe may be positioned between one spacer 240 and one heat spreader 550. In some embodiments, a spacer 240 may include two separate structures. The thickness of the spacer 240 may be of a minimum thickness at the distal region 242 of the spacer 240 and may increase in thickness extending in a proximal direction such that the spacer is of a maximum thickness at the proximal region 244 of the spacer 240. In this way, the spacer 240 may form a wedge-shaped structure. In any configuration, the spacer 240 may urge the proximal portion 234 of the heat pipe 230 closer to the inner surface of the housing 110 than the central portion 233 of the heat pipe 230. The central portion 233 may also be referred to as a curved portion.

FIG. 6 is a diagrammatic perspective view of a portion of an ultrasound probe housing 110, according to aspects of the present disclosure. FIG. 6 shows one structure which may be included in the housing 110 of the probe 108, or may be one half of the structure that forms the housing 110. Shown adhered to the inner surface of the housing 110 is a heat spreader material 550. As previously mentioned, the heat spreader material 550 may be laminated to the inner surface of the housing 110 or may be adhered by any other suitable means. The spreader 550 may be configured to maximize the surface area of contact between the spreader 550 and the inner surface of the housing 110 and may therefore extend along as much of the inner surface of the housing 110 as possible. The outer surface of the housing 110 shown may be configured to be grasped by a user of the ultrasound system 100.

The heat spreader film 550 may be die cut from bulk pyrolytic graphite sheet (PGS) having an integral pressure sensitive adhesive (PSA) on one face and a protective PET film laminated to the other face. The heat spreader 550 shape and relief cuts may be configured to maximize the surface area contact with the inner surface of the transducer housing 110. One heat spreader 550 may be applied to the inner surface of both the left and right housing halves 110 in such a way to eliminate or minimize wrinkles while maximizing wetted area to the housing 110.

To supplement the EMI RFI shield of the transducer probe 108, the PGS sheet of the heat spreader 550 may be connected to electrical shield potential by metallizing inner surfaces of the transducer housing using conductive paint or metal plating and utilizing an electrically conductive PSA adhesive on the PGS film. The housing 110 may form an electric and/or magnetic shield for the electronics 116 in the probe 108. This shield may include various conductive components positioned along the inner or outer surfaces of the housing 110. This shield may prevent various electromagnetic or radiofrequency signals from altering performance of various components within the probe 108. In some embodiments, the PGS sheet of the heat spreader 550 may be integrated into or be a component of this shield. In some embodiments, the heat spreader may be a die formed metal foil.

In some embodiments, the heat spreader material 550 may be attached to the inner surface of the housing 110 utilizing an electrically conductive PSA adhesive that allows the PGS to be part of the EMI RFI shielding circuit. In other embodiments, the heat spreader material 550 may not be attached with an electrically conductive PSA adhesive. Rather, a thin, soft, non-electrically conductive adhesive may be used. A thin non-electrically conductive adhesive may still permit electrical contact between the PGS sheet and the conductive coating and/plating on the inner surface of the housing (part of EMI RFI shielding circuit) when the PGS film is well wetted to the housing. The inner surface of the housing 110 may additionally include a metallized portion forming a shield for the electronics 116 within the probe 108 against electromagnetic interference and/or radiofrequency interference. The heat spreader 550 may be in electrical communication with this metallized portion of the housing 110. This may be done with the electrically conductive adhesive or by any other suitable means. Once the heat spreader 550 is adhered to the housing 110, the heat spreader 550 may form a portion of the electromagnetic shield. In some embodiments, the heat spreader material 550 may be a single sheet of material or may be many sheets of material. Several sheets may completely or partially overlap to form the heat spreader material 550.

Figure 7:
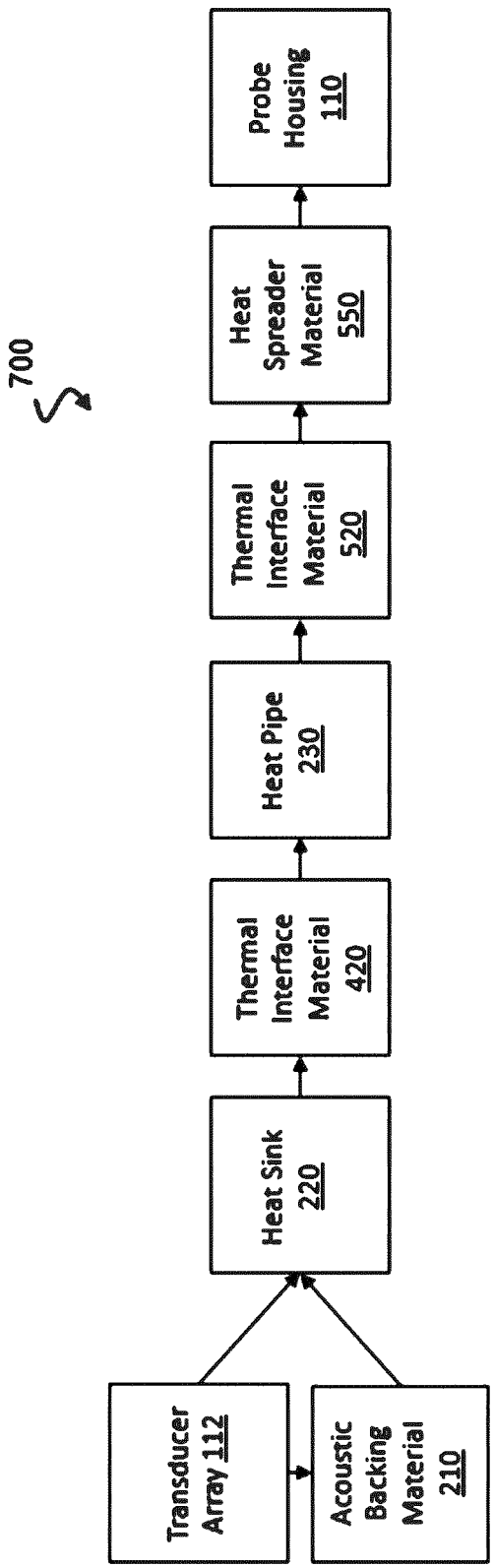
FIG. 7 is a schematic diagram of a thermal path through which heat dissipates from an ultrasound probe, according to aspects of the present disclosure.

FIG. 7 is a schematic diagram of the thermal path 700 through which heat may dissipate from the ultrasound probe 108, according to aspects of the present disclosure. It is noted that any of the components or steps along the thermal path 700 described may be modified and/or combined with other steps.

Heat may be generated by the transducer array 112, matching layers, the acoustic lens 310, acoustic backing material 210, or various other components within the probe 108. The heat generated by the transducer array 112 may be partially absorbed by the acoustic backing material 210 positioned directly behind the transducer array 112. The heat generated by the transducer array may then be transferred to the fins 226 of the heatsink 220. The heat may then pass through the heatsink 220 and be transferred to the heat pipes 230 in physical and/or thermal contact with the heatsink 220 through the thermal interface material 312. The heat may then pass through the heat pipes to the heat spreader material 550. The heat may pass through a thermal interface material 520. The heat may also or alternatively pass through a layer of thermal interface material as previously described with reference to FIG. 5. The heat may then be transferred from the heat spreader material 550 to the inner surface and/or the outer surface of probe housing 110 and from there into the surrounding environment. In this way, heat is dissipated away from the distal surface of the ultrasound probe 108 and keep the temperature of the surface which may often be brought into physical contact with a patient's skin within any regulatory temperature limits.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the claims.

What is claimed is:
1. An ultrasound imaging device, comprising:
 a housing comprising an outer surface and an inner surface, wherein the outer surface is configured to be grasped by a user;
 an array of acoustic elements configured to transmit ultrasound energy and receive ultrasound echoes associated with the ultrasound energy, wherein the array of acoustic elements is disposed at an end of the housing;
 a heat sink disposed within the housing and configured to receive heat generated by the array of acoustic elements;
 a heat pipe disposed within the housing and configured to transmit the heat away from the end of the housing, wherein the heat pipe comprises a proximal portion and a distal portion; and
 a heat spreader material disposed on the inner surface of the housing and configured to dissipate the heat, wherein the distal portion of the heat pipe is in thermal contact with the heat sink and the proximal portion of the heat pipe is in thermal contact with the heat spreader material, and wherein the heat pipe comprises a central portion between the proximal portion and the distal portion, and wherein the proximal portion and the distal portion comprise a flattened cross-sectional profile with a larger surface area for thermal contact, and the central portion comprises a non-flattened cross-sectional profile with a smaller surface area for thermal contact, the larger surface area relative to the smaller surface area.

2. The device of claim 1, wherein the heat pipe comprises a bent shape.

3. The device of claim 1, wherein the heat spreader material comprises pyrolytic graphite.

4. The device of claim 1, further comprising an electrically conductive adhesive configured to adhere the heat spreader material to the inner surface of the housing.

5. The device of claim 1, further comprising electronics in communication with the array of acoustic elements and disposed within the housing,
   wherein the inner surface of the housing comprises a metallized portion forming a shield for the electronics against at least one of electromagnetic interference or radiofrequency interference,
   wherein the heat spreader material is in electrical communication with the metallized portion via an electrically conductive adhesive such that the heat spreader material comprises a portion of the shield.

6. The device of claim 1, wherein the heat sink comprises a body and a plurality of fins extending from the body, wherein the plurality of fins is disposed between the array of acoustic elements and the body.

7. The device of claim 6, further comprising an acoustic backing material disposed on a backside of the array of acoustic elements, wherein the plurality of fins are embedded within the acoustic backing material.

8. The device of claim 6, further comprising a thermal interface material,
   wherein the distal portion of the heat pipe is in thermal contact with the body of the heat sink, and
   wherein the thermal interface material is disposed between the distal portion of the heat pipe and the body of the heat sink.

9. The device of claim 6,
   further comprising a mounting bracket,
   wherein the distal portion of the heat pipe is in thermal contact with the body of the heat sink,
   wherein the distal portion of the heat pipe is coupled to the mounting bracket, and
   wherein the mounting bracket is coupled to the body of the heat sink.

10. The device of claim 6,
    wherein the body of the heat sink comprises a curved portion,
    wherein the plurality of fins extend from the curved portion such that the plurality of fins comprise a curved profile.

11. The device of claim 1, further comprising:
    electronics in communication with the array of acoustic elements and disposed within the housing; and
    a spacer disposed between the electronics and the heat pipe, and configured to urge the proximal portion of the heat pipe closer to the inner surface of the housing than the central portion of the heat pipe.

12. The device of claim 1, further comprising a thermal interface material disposed between the proximal portion of the heat pipe and the inner surface of the housing.

13. The device of claim 1, further comprising an additional heat pipe,
    wherein the housing comprises a first portion coupled to a second portion,
    wherein the proximal portion of the heat pipe is in thermal contact with the inner surface of the first portion of the housing, and
    wherein a proximal portion of the additional heat pipe is in thermal contact with the inner surface of the second portion of the housing.

\* \* \* \* \*